United States Patent [19]
Pfahl et al.

[11] Patent Number: 5,712,093
[45] Date of Patent: *Jan. 27, 1998

[54] RXR HOMODIMER FORMATION

[75] Inventors: Magnus Pfahl, Solana Beach; Xiao-kun Zhang, La Jolla, both of Calif.

[73] Assignee: The Burnham Institute, La Jolla, Calif.

[*] Notice: The term of this patent shall not extend beyond the expiration date of Pat. No. 5,552,271.

[21] Appl. No.: 297,706

[22] Filed: Aug. 29, 1994

Related U.S. Application Data

[63] Continuation of Ser. No. 901,719, Jun. 16, 1992.

[51] Int. Cl.$^6$ .............................. C12Q 1/68; G01N 33/53
[52] U.S. Cl. ................................................ 435/6; 435/7.1
[58] Field of Search ...................... 435/6, 24.1; 436/177, 436/806, 815; 530/350

[56] References Cited

FOREIGN PATENT DOCUMENTS

WO 93/21146  10/1993  WIPO.

OTHER PUBLICATIONS

Mangelsdorf, D.J. et al 1990 "Nuclear Receptor that Identifies a Novel Retinoic acid Response Pathway" Nature 345:224.

Bugge et al., "RXRα, A Promiscuous Partner of Retinoic Acid and Thyroid Hormone Receptors," *The EMBO Journal* 11:1409–1418 (1992).

Heyman et al., "9-Cis Retinoic Acid is a High Affinity Ligand for the Retinoid X Receptor," *Cell* 68:397–406 (1992).

Kliewer et al., "Retinoid X Receptor Interacts with Nuclear Receptors in Retinoic Acid, Thyroid Hormone and Vitamin D$_3$ Signalling," *Nature* 355:446–449 (1992).

Leid et al., "Purification, Cloning, and RXR Identity of the HeLa Cell Factor with which RAR or TR Heterodimerizes to Bind Target Sequences Efficiently," *Cell* 68:377–395 (1992).

Mangelsdorf et al., "A Direct Repeat in the Cellular Retinoid–Binding Protein Type II Gene Confers Differential Regulation by RXR and RAR," *Cell* 66:555–561 (1991).

Mangelsdorf et al., "Characterization of three RXR Genes that Mediate the Action of 9–cis Retinoic Acid," *Genes & Development* 6:329–344 (1992).

Marks et al., "H–2RIIBP (RXRβ) Heterodimerization Provides a Mechanism for Combinatorial Diversity in the Regulation of Retinoic Acid and Thyroid Hormone Responsive Genes," *The EMBO Journal* 11:1419–1435 (1992).

Oro et al., "Relationship Between the Product of the *Drosphilia Ultraspiracle* Locus and the Vertebrate Retinoid X Receptor," *Nature* 347:298–301 (1990).

Rottman et al., "A Retinoic Acid–Responsive Element in the Apolipoprotein AI Gene Distinguishes Between Two Different Retinoic Acid Response Pathways," *Molecular and Cellular Biology* 11:3814–3820 (1991).

Tora et al., "The Human Estrogen Receptor has Two Independent Nonacidic Transcriptional Activation Functions," *Cell* 59:477–487 (1989).

Tzukerman et al., "The Human Estrogen Rceptor has Transcriptional Activator and Repressor Functions in the Absence of Ligand," *The New Biologist* 2:613–620 (1990).

Yu et al., "RXRβ: A Coregulator that Enhances Binding of Retinoic Acid, Thyroid Hormone, and Vitamin D Receptors to their Cognate Response Elements," *Cell* 67:1251–1266 (1991).

*Primary Examiner*—David Guzo
*Assistant Examiner*—Robert Schwartzman
*Attorney, Agent, or Firm*—Campbell & Flores

[57] ABSTRACT

The invention provides a method of screening a substance for the ability to affect the formation of a retinoid X receptor homodimer comprising combining the substance and a solution containing retinoid X receptors and determining the presence of homodimer formation. Also provided is a method of screening a substance for an effect on a retinoid X receptor homodimer's ability to bind DNA comprising combining the substance with the homodimer and determining the effect of the compound on the homodimer's ability to bind DNA. A method of inhibiting an activity of a retinoid X receptor heterodimer comprising increasing the formation of a retinoid X receptor homodimer, thereby preventing the retinoid X receptor from forming a heterodimer and preventing the resulting heterodimer activity is also provided. A method of inhibiting an activity of a retinoid X receptor homodimer is also provided. A method of determining an increased probability of a pathology associated with retinoid X receptor homodimer formation and treating such pathology are further provided. Finally a method of screening a response element for binding to a retinoid X receptor homodimer is provided.

8 Claims, 12 Drawing Sheets

| | |
|---|---|
| TREpal | gatcTCAGGTCATGACCTGAgatc<br>ctagAGTCCAGTACTGGACTctag |
| ApoAI-RARE | gatcAGGGCAGGGGTCAAGGGTTCAGTgatc<br>ctagTCCCGTCCCCAGTTCCCAAGTCActag |
| CRBPII-RARE | gatcCAGGTCACAGGTCACAGGTCACAGTTCAAgatc<br>ctagGTCCAGTGTCCAGTGTCCAGTGTCAAGTTctag |
| βRARE | gatctGTAGGGTTCACCGAAAGTTCACTCagatc<br>ctagaCATCCCAAGTGGCTTTCAAGTGAGtctag |
| CRBPI-RARE | gatccAGGTCAAAAAGTCAGggatc<br>ctaggTCCAGTTTTTCAGTCcctag |
| MHC-TRE | gatcCTGGAGGTGACAGGAGGACAGCgatc<br>ctagGACCTCCACTGTCCTCCTGTCGctag |
| ME-TRE | gatcCAGGACGTTGGGGTTAGGGGAGGACAGTGGgatc<br>ctagGTCCTGCAACCCCAATCCCCTCCTGTCACCctag |
| DR-4 | gatcTCAGGTCATCTCAGGTCAgatc<br>ctagAGTCCAGTAGAGTCCAGTctag |
| DR-5 | gatcTCAGGTCATCCTCAGGTCAgatc<br>ctagAGTCCAGTAGGAGTCCAGTctag |
| ERE | gatcTCAGGTCACTGTGACCTGAgatc<br>ctagAGTCCAGTGACACTGGACTctag |

FIG.3a

☐ no retinoid    ▨ all-trans RA    ■ 9-cis RA

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg Tyr Lys Asp Asp Asp Asp Lys
1                 5

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATCAGGCAG GGGTCAAGGG TTCAGTGATC        30

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GATCCAGGTC ACAGGTCACA GGTCACAGTT CAAGATC        37

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATCTGATAG GGTTCACCGA AAGTTCACTC AGATC        35

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GATCCAGGTC AAAAAAGTCA GGATC 25

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATCCTGGAG GTGACAGGAG GACAGCGATC 30

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GATCCAGGAC GTTGGGGTTA GGGGAGGACA GTGGGATC 38

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GATCTCAGGT CATCTCAGGT CAGATC 26

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GATCTCAGGT CATCCTCAGG TCAGATC 27

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATCTCAGGT CACTGTGACC TGAGATC 27

( 2 ) INFORMATION FOR SEQ ID NO:11:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:11:

GATCTCAGGT CATGACCTGA GATC  24

RXR HOMODIMER FORMATION

This application is a continuation, of application Ser. No. 07/901,719, filed Jun. 16, 1992.

This invention was made with government support under Grant Numbers CA51993 and CA50676 from the National Institutes of Health. The U.S. Government may have certain rights in this invention.

BACKGROUND OF THE INVENTION

The vitamin A metabolite all-trans-retinoic acid (RA) and its natural and synthetic derivatives (retinoids) exert a broad range of biological effects[1,2]. Clinically, retinoids are important therapeutics in the treatment of skin diseases and cancers[3-6]. Understanding how the multitude of retinoid actions can be mediated at the molecular level has been greatly enhanced by the cloning and characterization of specific nuclear receptors, the retinoic acid receptors (RARs)[7-12] and the retinoid X receptors (RXRs)[13-17]. RARs and RXRs are part of the steroid/thyroid hormone receptor superfamily[18,19]. Both types of receptors are encoded by three distinct genes, $\alpha$, $\beta$, and $\gamma$, from which, in the case of RARs, multiple isoforms can be generated[20-22]. Interestingly, while RARs are specific to vertebrates, the RXRs have been well conserved from Drosophila to man[17,23]. Despite the considerable advances in the understanding of the molecular mechanisms of retinoid receptor action in recent years, a central question of whether distinct molecular pathways for naturally occurring retinoids exist has not yet been answered. The recent observation that the RA stereoisomer 9-cis-RA binds with high affinity to RXRs[23,24] suggested a retinoid response pathway distinct from that of all-trans-RA. However, it was almost simultaneously discovered by several laboratories that RARs require interaction with auxiliary receptors for effective DNA binding and function and that RXRs are such auxiliary receptors[15,16,26-29]. Hence, RARs appear to function effectively only as heterodimeric RAR/RXR complexes, or in combination with comparable auxiliary proteins that still need to be identified. Similarly, RXRs were shown to require RARs, thyroid hormone receptors (TRs), or Vitamin $D_3$ receptors (VDRs) for effective DNA binding[15,16,26-29]. Thus, from these DNA binding studies, RXRs appeared to be able to function predominantly if not exclusively as auxiliary receptors, thereby playing a crucial role in generating a high degree of diversity and specificity of transcriptional controls and mediating the highly pleiotropic effects of different hormones by increasing DNA affinity and specificity for at least 3 different classes of ligand activated receptors.

Contrary to these findings, the present invention provides that RXRs form homodimers. The invention provides that these homodimers effectively bind to specific response elements in the absence of auxiliary receptors and their DNA binding specificity is distinct from that of the RXR containing heterodimers. The invention demonstrates a novel mechanism for retinoid action by which a ligand induced homodimer mediates a distinct retinoid response pathway.

SUMMARY OF THE INVENTION

The invention provides a method of screening a substance for the ability to affect the formation of a retinoid X receptor homodimer comprising combining the substance and a solution containing retinoid X receptors and determining the presence of homodimer formation. Also provided is a method of screening a substance for an effect on a retinoid X receptor homodimer's ability to bind DNA comprising combining the substance with the homodimer and determining the effect of the compound on the homodimer's ability to bind DNA. A method of inhibiting an activity of a retinoid X receptor heterodimer comprising increasing the formation of a retinoid X receptor homodimer, thereby preventing the retinoid X receptor from forming a heterodimer and preventing the resulting heterodimer activity is also provided. A method of inhibiting an activity of a retinoid X receptor homodimer is also provided. A method of determining an increased probability of a pathology associated with retinoid X receptor homodimer formation and treating such pathology are further provided. Finally, a method of screening a response element for binding with a retinoid X receptor homodimer is provided.

(a) In vitro synthesized RXRα was incubated either with (+) or without (−) indicated hormones ($10^{-7}$M 9-cis-RA; $10^{-6}$M RA; $10^{-6}$M $T_3$) in the presence or absence of in vitro synthesized TRα or RARβ for 30 min at room temperature. After this preincubation, the reaction mixtures were analyzed by gel retardation assay using $^{32}$P-labeled TREpal as probe. Lane 1 represents the nonspecific binding of unprogrammed reticulocyte lysate. Open triangles indicate the nonspecific complex observed with unprogrammed reticulocyte lysate. Solid triangles indicate the specific TRα-RXRα heterodimer binding. Arrows indicate specific RXRα a homodimer binding. The RXRα/RARβ heterodimer migrates at the same position as the RXRα homodimer. For comparison, the effect of 9-cis-RA on RARβ binding is shown.

(b) To determine that 9-cis-RA induced DNA binding complex contains RXRα protein, Flag-RXRα (F-RXR), an RXRα derivative that contains an eight-amino-acid epitope (Flag) at its amino terminal end which can be recognized by a specific anti-Flag monoclonal antibody, was constructed. In vitro synthesized F-RXRα was incubated either with (+) or without (−) $10^{-7}$M 9-cis-RA in the presence of either specific anti-Flag antibody (αF) or nonspecific preimmune serum (NI) for 30 min at room temperature. The effect of anti-Flag antibody on F-RXRα binding in the presence of 9-cis-RA was then analyzed by gel retardation assay using $^{32}$P-labeled TREpal as a probe. Lane 1 represents the nonspecific binding of unprogrammed reticulocyte lysate (open triangles). Arrows indicates the specific F-RXRα homodimer and RAR-RXR heterodimer binding. Diamond indicates the anti-Flag antibody up-shifted F-RXR homodimer.

Figure 2A:
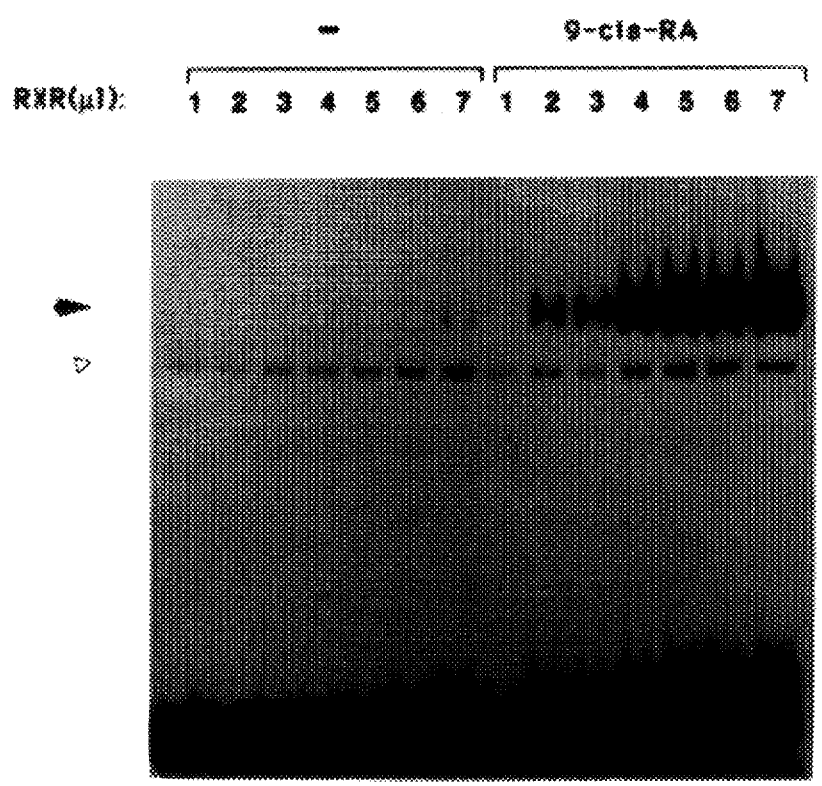
Figure 2B:
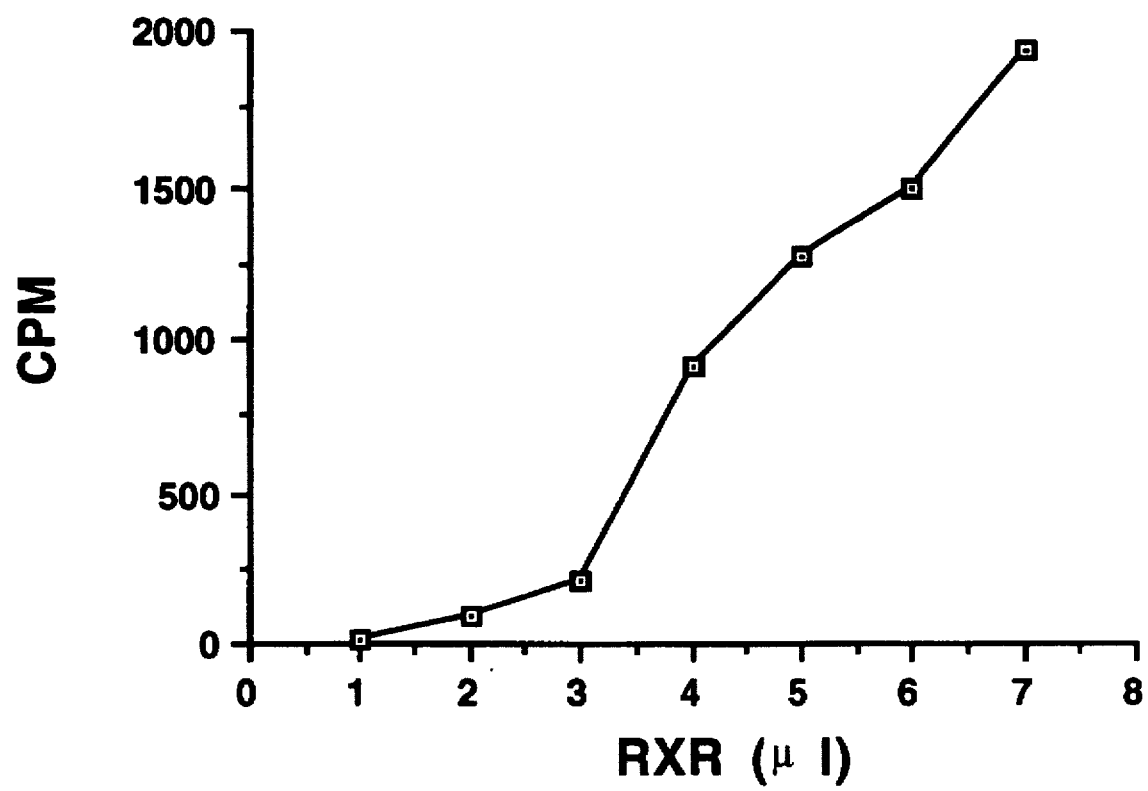

FIG. 2 shows the characterization of 9-cis-RA induced RXR homodimer on TREpal.

(a) Cooperative binding of 9-cis-RA induced RXRα homodimer. Formation of RXR-DNA complex at different receptor concentrations in the absence or presence of $10^{-7}$M 9-cis-RA was analyzed by gel retardation assay using labeled TREpal as probe. Open triangle indicates the nonspecific binding of an unprogrammed reticulocyte lysate. Arrows indicate the specific RXR binding complex.

(b) Quantitation of the RXR binding complex at different receptor concentrations in the presence of 9-cis-RA. Gel slices containing RXR binding complex in the presence of 9-cis-RA shown in FIG. 2(a) were excised and counted in a scintillation counter and plotted.

(c) 9-cis-RA concentration dependent binding of RXR homodimer on TREpal. Equal amounts of in vitro synthesized RXR protein were incubated with indicated concentrations of 9-cis-RA. The reaction mixtures were then analyzed by gel retardation assay using labeled TREpal as a probe. Open triangles indicate the nonspecific binding of unprogrammed reticulocyte lysate. Arrows indicate the specific RXR binding complex.

FIG. 3 shows 9-cis-RA induces RXR homodimer binding on RXR specific response elements.

(a) Nuclear receptor binding elements used in this study. These oligonucleotides were synthesized with appropriate restriction sites at both ends as indicated by the small letters. Sequences that are closely related to the AGG/TTCA motif are indicated by arrows.

Figure 1A:
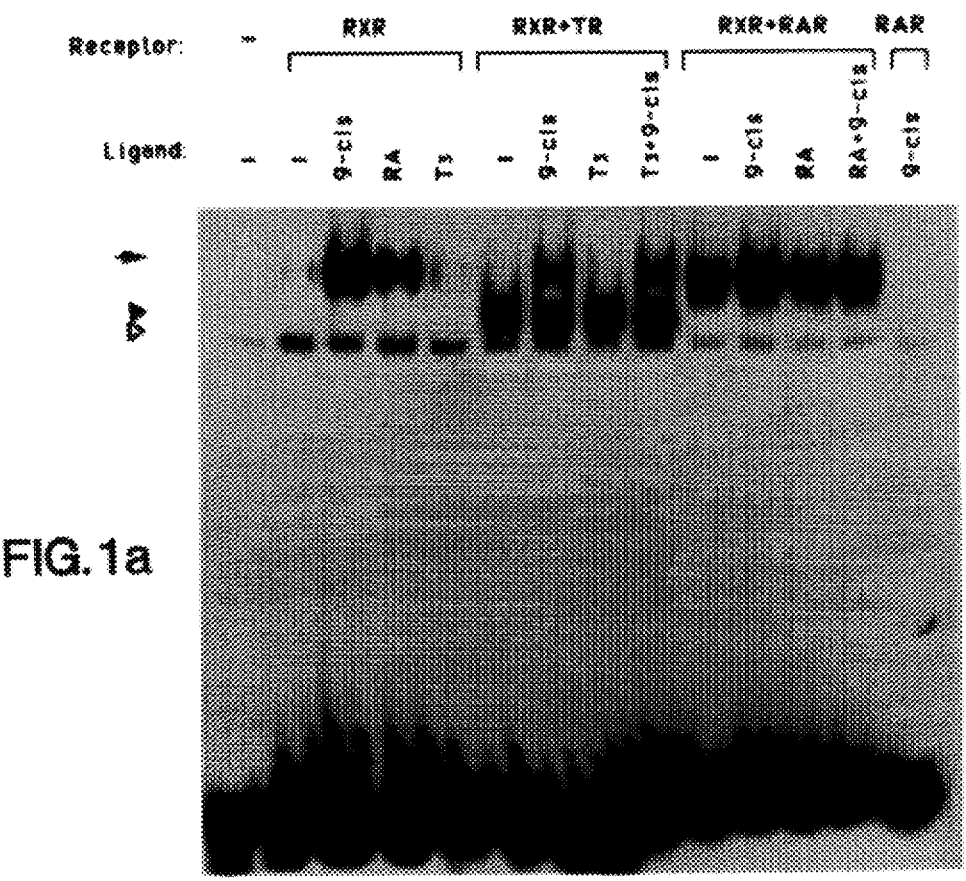
FIG. 1 shows 9-cis retinoic acid induces RXR homodimer binding on TREpal.

(b) The effect of 9-cis-RA on RXR homodimer binding of ApoAI-RARE or CRBPII-RARE was analyzed essentially as described in FIG. 1a. Lane 1 represents the nonspecific binding of unprogrammed reticulocyte lysate which are indicated by the open triangles. Solid triangles indicate the RAR/RXR heterodimer complex. Arrows indicate the specific RXR binding complex.

FIG. 4 shows response element specific binding of RXR homodimer. The effect of 9-cis-RA on RXR binding on RA specific response elements (a), $T_3$ specific response elements (b), or estrogen specific response element (c) was analyzed by gel retardation assays as described in FIG. 1a. For comparison, the binding of RXR/RAR heterodimer (a), RXR/TR heterodimer (b) or estrogen receptor (c) is shown. Open triangles indicate the nonspecific binding of unprogrammed reticulocyte lysate. Solid triangle indicates the RAR/RXR heterodimer complex (a), TR/RXR heterodimer complex (b) or ER complexes (c).

Figure 5:
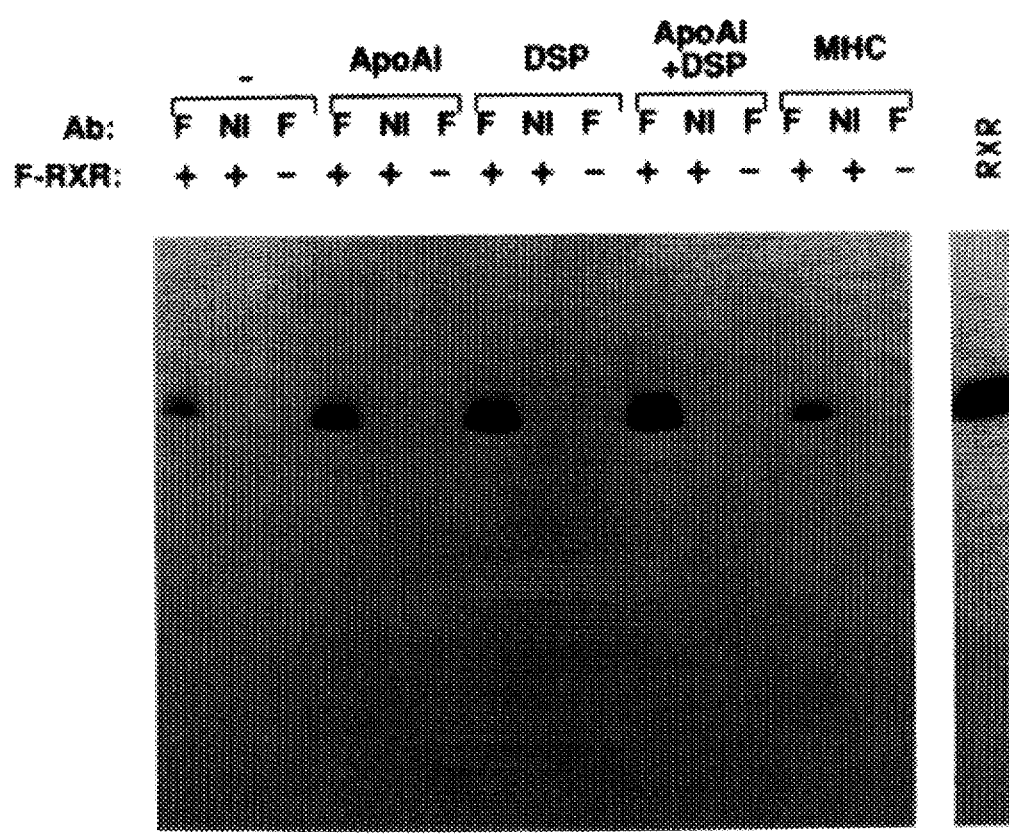

FIG. 5 shows RXR homodimerization occurs in solution. $^{35}$S-labeled in vitro synthesized RXRα proteins was incubated with partially purified bacterially expressed Flag-RXR (F-RXR) (+) or similarly prepared glutathione transferase control protein (−) either in the presence or absence of response elements or chemical cross-linker DSP as indicated. After incubation, either anti-Flag antibody (F) or nonspecific preimmune serum (NI) was added. $10^{-7}$M 9-cis-RA was maintained during working process. The immune complexes were washed in the presence of $10^{-7}$M-cis-RA, boiled in SDS sample buffer and separated on a 10% SDS-PAGE. The $^{35}$S-labeled in vitro synthesized RXRα protein is shown in the right panel.

FIG. 6 shows transcriptional activation of RXR and RARα: RXR heterodimers by 9-cis RA on natural response elements. CV-1 cells were contransfected with 100 ng of the reporter plasmids (a) TREpal-tk-CAT (b) βRARE-tk-CAT (c) ApoAI-RARE-tk-CAT and (d) CRBPI-RARE-tk-CAT and 5 ng of empty pECE expression vector, pECE-RXRα, pECE RARα or combination of both as indicated. Transfected cells were treated with no hormone (open bars), $10^{-7}$M RA (shadowed bars) or $10^{-7}$M 9-cis-RA (dark shadowed bars). The results of a representative experiment performed in duplicate are shown.

DETAILED DESCRIPTION OF THE INVENTION

The invention provides a method of screening a substance for the ability to affect the formation of an RXR homodimer comprising combining the substance and a solution containing RXRs and determining the presence of a homodimer formation. The presence of homodimer formation can, for example, be determined by detecting the activation of transcription by the RXR homodimer or by coprecipitation. The affect can be the induction of homodimer formation, for example, an activity similar to that activated by 9-cis-RA. The affect can also be the inhibition of homodimer formation. Examples of inhibition include a substance which binds 9-cis-RA to block its activity. Such screening of substances is routinely carried out given the subject discovery of homodimer formation. In particular assays set forth below can generally be used for screening by merely substituting the substance of interest for 9-cis-RA. A good starting point for screening such "substances" is the activity of 9-cis-RA described herein. The constituents on 9-cis-RA can be varied and screened in the method to determine any increase or decrease in homodimer formation. However, any substance can be screened in this assay to determine any affect on homodimer formation.

The data set forth herein utilizes RXR. However, given the high homology between RXRα, β and γ, each protein should form homodimers and have the activity described for RXRα homodimers. Relatedly, homodimers can form between different RXRs. For example, homodimers can form between RXRα and RXRβ or between RXRβ and RXRγ or between RXRα and RXRγ. The activity of these homodimers can be confirmed using the methods set forth herein.

The invention also provides a method of screening a substance for an effect on an RXR homodimer's ability to bind DNA comprising combining the substance with the homodimer and determining the effect of the compound on the homodimer's ability to bind DNA. For example, compounds which might bind the homodimer or bind the DNA response element recognized by an RXR homodimer can be screened in this method.

The invention further provides a method of inhibiting an activity of an RXR-containing heterodimer comprising increasing the formation of an RXR homodimer, thereby preventing the RXR from forming a heterodimer and preventing the resulting heterodimer activity. The activity can be any activity but is generally the activation or repression of transcription. The activity can be blocked, for example, by utilizing RXRs to form homodimers which otherwise would be available to form heterodimers. Since the number of heterodimers are decreased, the activity of the heterodimers is decreased. In one example, the RXR heterodimer is comprised of thyroid hormone receptor and RXR. The activity of the RXR/TR heterodimer was decreased. Other heterodimers can be tested using standard methods.

The invention also provides a method of inhibiting an activity of an RXR receptor homodimer comprising preventing the formation of the RXR homodimer. Such inhibition can be obtained, for example, by inhibiting 9-cis-RA or the transcription of 9-cis-RA. The activity inhibited is generally the activation or repression of transcription.

The invention also provides a method of inhibiting an activity of an RXR homodimer comprising preventing the binding of the RXR homodimer to its response element. For example, the activity of a receptor which competes for the same response element can be promoted. In general, the activity which is inhibited is the activation or repression of transcription.

The invention still further provides a method of determining an increased probability of a pathology associated with RXR homodimer formation comprising detecting a decrease of RXR homodimer formation in the subject when compared to a normal subject. Such a decrease can result, for example, by a mutated RXR. The decrease can be detected by an assay for the homodimers in a sample or by detecting mutations known to decrease homodimer formation.

Relatedly, the invention provides a method of treating a pathology associated with decreased RXR homodimer formation in a subject comprising increasing the amount of RXR capable of forming a homodimer in the subject. Such an increase can be accomplished, for example, utilizing compounds which promote RXR transcription. The pathology can be associated with the skin, e.g., acne and psoriasis.

The invention also provides a purified RXR homodimer. By "purified" is meant free of at least some of the cellular contaminants associated with RXR homodimers in a natural environment.

Finally, the invention provides a method of screening a response element for binding with a RXR homodimer comprising combining the response element with the RXR homodimer and detecting the presence of binding. The presence of binding can be determined by a number of standard methods. In one method, binding is detected by the transcriptional activation of a marker which is operably linked to the response element. By "operably linked" is meant the marker can be transcribed in the presence of the transcriptional activator.

The invention grows out of our study of the effects of the natural vitamin A derivative 9-cis-RA on retinoid receptor DNA binding and transcriptional activation. In contrast to all-trans-RA, the 9-cis derivative dramatically enhances RXR$\alpha$ binding at $10^{-9}$ to $10^{-8}$M concentrations to several RXR specific RAREs but not to natural TREs or the ERE. The effect is specific to RXR since 9-cis-RA did not induce binding of RAR$\alpha$, $\beta$ or $\gamma$ to response elements (FIG. 1, FIG. 3). Judging from the migration pattern in the gel shift assays, we assume that 9-cis-RA induces homodimer formation, although a larger complex containing an RXR trimer or tetramer can occur (particularly in the case of the CRBPII-RARE). Such trimer or tetramer formation can be tested using the methods set forth herein.

RXR$\alpha$ homodimers exert response element specificity distinct from heterodimers. The rCRBPI response element did not interact with RXR homodimers, while the CRBPII response element 0 the only natural RARE identified so far that contains perfect repeats—was a strong binder of 9-cis-RA induced RXR$\alpha$ homodimers. It has been shown previously that this response element is well activated by RXR$\alpha$[24,30]. Although this response element is also bound effectively by the RXR$\alpha$-RAR$\alpha$ heterodimer (FIG. 3)[27,29], the heterodimer appears to have a repressor function[30].

The results obtained with the transcriptional activation studies agree well with the DNA binding studies although CV-1 cells like all other mammalian tissue culture cells tested, contain endogenous retinoid receptors that can partially obscure effects. Nonetheless, response elements that strongly bound 9-cis-RA-RXR$\alpha$ homodimers also responded strongly to contransfected RXR$\alpha$ in the presence of 9-cis-RA whereas response elements that did not bind well to RXR$\alpha$ homodimers like the rCRBPI-RARE or the MHC-TRE could not be activated by RXR$\alpha$ alone.

It is generally believed that the dimerization—homodimerization or heterodimerization—of nuclear hormone receptors is critical for high affinity interaction of a receptor with their cognate response elements. RXRs exist mainly as monomer in solution[16] and require high concentrations or the presence of RARs, TRs or VDR to display effective DNA binding activity[13,15,16,26-30]. The observation of the enhanced cooperative RXR DNA binding activity in the presence of 9-cis-RA demonstrates that 9-cis-RA induced the formation of RXR homodimers which have an increased affinity for DNA. Thus, binding of 9-cis-RA to RXR can induce a conformational change, which allows homodimerization to occur. It is interesting that although 9-cis-RA and RA can bind to RAR,[24,25] they do not induce RAR homodimer formation.

RXR$\alpha$ homodimer formation can occur in solution in the absence of DNA. Thus, when 9-cis becomes available to cells, the equilibrium between monomeric and dimeric receptors is changed and an additional species, the RXR homodimer can be formed, allowing for novel response pathways. The concept of ligand induced homodimer binding as observed by in vitro gel shift assay has not been previously observed for nuclear receptors with the exception of a mutated estrogen receptor (ER-val-400)[43,44].

For the related TRs, a ligand effect has been reported on homodimer binding, [45,46] however the ligand (T3) reduced homodimer response element interaction. Since the carboxyterminal half of TRs and RARs encodes both ligand as well as dimerization functions[35,45,47], a strong effect of the ligand on dimerization as observed here is not completely surprising. However, the specificity of the effect is quite dramatic since only homodimer but not heterodimer formation appears to be affected. An overall picture emerges where the carboxyterminal region of receptors through its intermixed domains (that also includes a transcriptional activation region)[48] allows for multiple activities of individual receptors that may also include interactions with other regulatory proteins[49].

The data presented in this application clearly demonstrate the central role of the RXRs, having dual functions that allow them to act as auxiliary receptors for three classes of hormone receptors, the RARs, TRs and VDRs through heterodimerization. The two functions of RXR—homodimerization and heterodimerization—represent two distinct transcriptional regulatory controls that can be expected to affect distinct physiological processes. Thus, 9-cis-RA can have therapeutic properties distinct from that of all-trans RA.

9-cis induces RXR homodimer binding on the TREpal

Although RXRs have been shown to bind RA response elements (RAREs) when used at high concentrations,[28,30,31] more recent investigations revealed that RXR exists mainly as monomers in solution[10] and that effective DNA interaction requires heterodimer formation with RARs or TRs or VDR[15,16,26-29]. Binding of the heterodimers to a variety of response elements was found to be ligand independent[32]. The newly discovered natural RA isomer, 9-cis-RA, has been reported to be an effective activator of RXRs in Drosophila Schneider cells that are known to contain neither RAR nor TRs[17,24]. If 9-cis-RA is indeed a true ligand for RXRs, one might expect that this ligand modulates RXR response element interaction. We therefore investigated the effect of 9-cis-RA on RXR$\alpha$ binding to the palindromic TRE (TREpal), an RXR responsive element[14], in the absence and presence of coreceptors (TRs and RARs).

The cloning of the receptor cDNAs for RXR$\alpha$, RAR$\beta$, or TR$\alpha$ into the pBluescript (Stratagene, San Diego, Calif.) have been described previously [26]. Flag-RXR$\alpha$ was constructed as described previously[33] by ligation of a double-stranded oligonucleotide containing an ATG codon and a DNA sequence encoding Flag (Arg-Tyr-Lys-Asp-Asp-Asp-Asp-Lys) [SEQ ID NO1] to the N-terminus of RXR$\alpha$. The fusion product was then cloned into pBluescript. The synthesis of receptor proteins using in vitro transcription/translation system and gel retardation assays using synthesized receptor proteins and the double-stranded TREpal[34] were as described[33]. 9-cis-RA (m.p. 184°–187° C.) was prepared from 9-cis-retinal by a two-step sequence of $MnO_2$ oxidation in the presence of HOAc-MeOH to give the methyl ester (69%) followed by hydrolysis (80%) in 0.5N KOH in 25% aq. MeOH and crystallization (MeOH); HPLC (Novapak $C_{18}$, 32% MeCN, 27% MeCH, 16% APrOH, 24% $H_2O$, 1% HOAc, 1.9 mL/min, 260 nM) $t_R$ 15.4 min (100%). To analyze the effect of hormones, the receptor proteins were incubated with appropriate concentrations of hormone at room temperature for 30 min before performing the DNA binding assay. When anti-Flag antibody (Immunex, Seattle, Wash.) was used, 1 µl of the antiserum was incubated with receptor protein for another 30 min at room temperature before performing the DNA binding assay.

While in the absence of ligand RXR alone did not bind effectively to the TREpal and required TR or RAR for response element interaction, binding of RXR was dramatically increased in the presence of 9-cis-RA (FIG. 1a) and did not require TRs or RARs. The RXR specific band observed in the presence of 9-cis-RA was as prominent as the bands obtained with the heterodimeric TR-RXR and RAR-RXR complexes. The RXR complex migrated more slowly than the TR-RXR complex at a position very similar to that of the RAR-RXR heterodimer-TREpal complex. These data therefore demonstrate that 9-cis-RA induces RXR homodimer formation. Due to migration of the RAR-RXR complex at the same position as the 9-cis-RA induced RXR homodimer complex, we were unable to determine in this experiment whether both complexes were formed. Remarkably, all-trans-RA when added at a concentration of $10^{-6}M$, also induced to some degree RXRα homodimer binding whereas $T_3$ did not. Although the RA effect could be observed with several freshly prepared RA solutions, it is not clear at this point whether this homodimer formation in the presence of RA is due to 9-cis-RA impurities in the all-trans-RA solutions used here, or is a direct effect of all-trans-RA (see below). Interestingly, although it was reported that 9-cis-RA is capable of binding to RAR[24], unlike its effect on RXR, 9-cis-RA was not found to induce RAR homodimer binding to the TREpal.

Figure 1B:
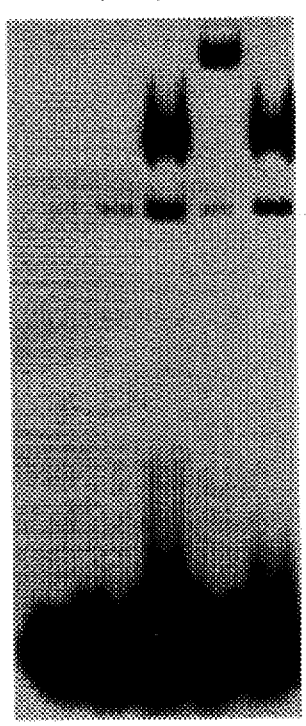
Figure 2C:
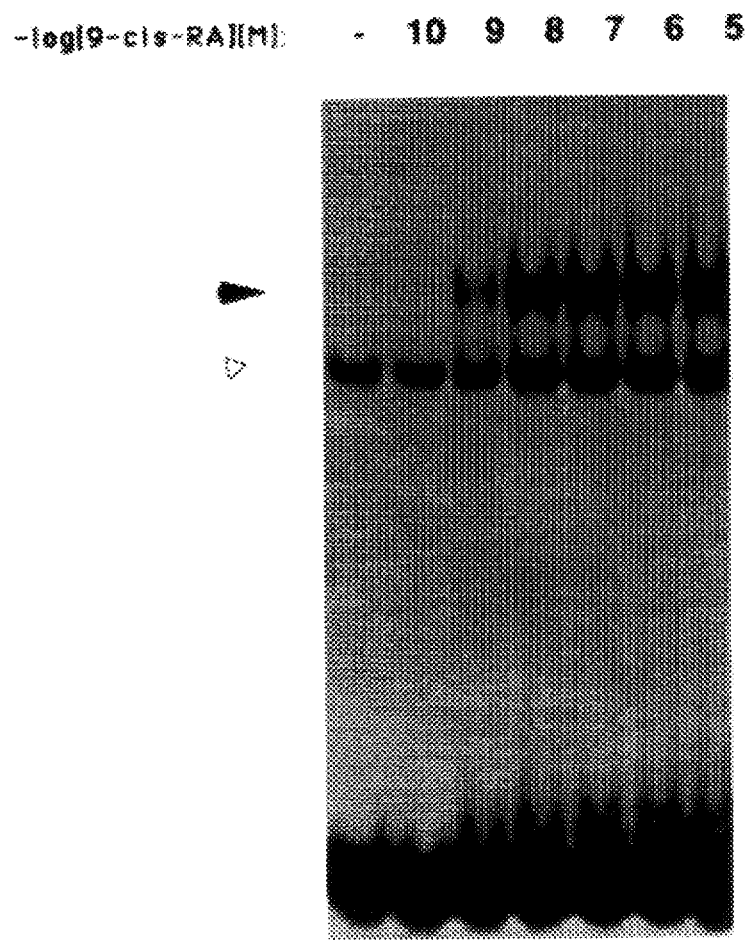

To provide further evidence that the observed complex in the presence of 9-cis-RA indeed was an RXR complex, we performed the DNA binding experiment with Flag-RXR, a derivative that carries an 8 amino acid aminoterminal epitope recognized specifically by anti-Flag (αF) antibody[33]. As shown in FIG. 1b, αF supershifted the 9-cis-RA induced complexes, while a nonspecific antibody did not. This proves that the complex observed with the TREpal in the presence of 9-cis-RA indeed contained RXR protein. To examine how dependent the 9-cis-RA induced homodimer formation is on the concentration of RXR protein, increasing concentrations of in vitro translated RXR protein were mixed with the labeled TREpal in the presence or absence of 9-cis-RA (FIG. 2a). When these mixtures were analyzed by the gel retardation assay, a strong cooperative effect in homodimeric DNA binding was seen, positively dependent on the RXRα protein concentration (FIG. 2a,b). Although slight binding of RXR can be observed when high concentrations of RXR were used, 9-cis-RA was required for efficient complex formation at all receptor concentrations used. We further determined the concentrations of 9-cis-RA required for homodimer complex formation at all receptor concentrations used. We further determined the concentrations of 9-cis-RA required for homodimer complex formation and observed a significant effect already at $10^{-9}M$ while optimal binding was seen at $10^{-8}M$ (FIG. 2c). Thus, effective RXR homodimer DNA interaction is dependent on RXR protein concentration and can occur at low levels of 9-cis-RA.

9-cis induced homodimeric interaction with specific response elements RXR containing heterodimers have a highly specific interaction with various natural response elements in that TR-RXR heterodimers only bind strongly to TREs but not to RAREs, whereas the opposite is true for RAR-RXR heterodimers[15,32]. We examined the sequence requirement of DNA binding of 9-cis-RA induced RXR homodimer using a number of natural and synthetic response elements (FIG. 3a).

Gel retardation assays using in vitro synthesized receptor protein are described in the FIG. 1 legend. The following oligonucleotides and their complements were used as probes in FIGS. 3 and 4. ApoAI-RARE, a direct repeat response element with 2 bp spacer[31], gatcAGGCAGGGGT-CAAGGGTTCAGTgatc [SEQ ID NO2]; CRBPII-RARE, a direct repeat RXR specific response element with 1 bp spacer[36], gatcCAGGTCACAGGTCACAGGTCA-CAGTTCAAgatc [SEQ ID NO3]; βRARE, a direct repeat of RA response element present in RARFβ promoter[35,36], gatcTGATAGGGTTCACCGAAAGTTCACTCagatc [SEQ ID NO4]; CRBPI-RARE, a direct repeat RA specific response element present in rat CRBPI promoter[37], gatc-cAGGTCAAAAAAGTCAGgatc [SEQ ID NO5]; MHC-TRE, a direct repeat $T_3$ specific response element present in rat α-myosin heavy chain gene[39], gatcCTGGAGGTGA-CAGGAGGACAGCgatc [SEQ ID NO6]; ME-TRE, a direct repeat $T_3$ specific response element present in the rat malic enzyme gene[40], gatcCAGGACGTTGGGGTTAGGGGAG-GACAGTGGgatc [SEQ ID NO7]; DR-4, an idealized direct repeat $T_3$ specific response element with 4 bp spacer[36], gatcTCAGGTCATCTCAGGTCAgatc [SEQ ID NO8]; DR-5, an idealized direct repeat RA specific response element with 5 bp spacer[38], gatcTCAGGTCATCCTCAGGT-CAgatc [SEQ ID NO9]; ERE, a perfect pal indromic ER response element[41], gatcTCAGGTCACTGTGACCT-GAgatc [SEQ ID NO10]. The sequence of TREpal [SEQ ID NO 11] is shown for comparison.

Figure 3B:
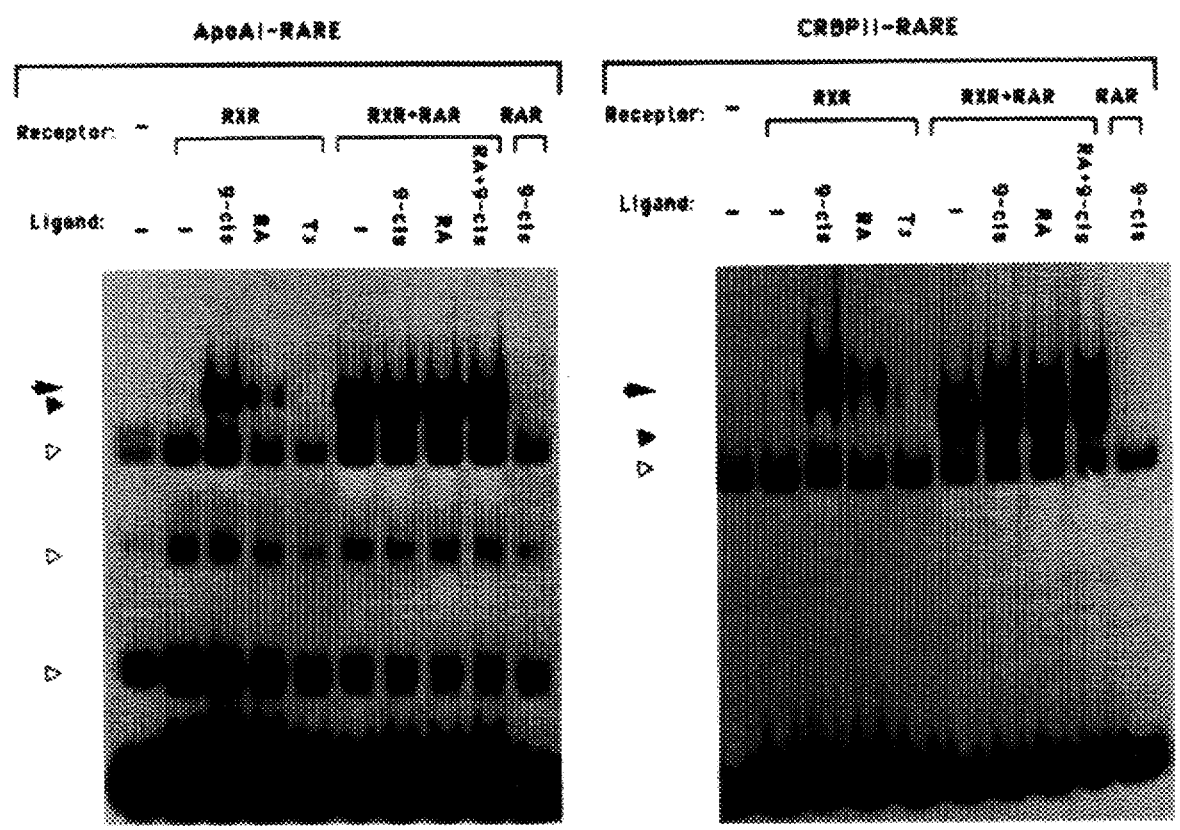
Figure 4A:
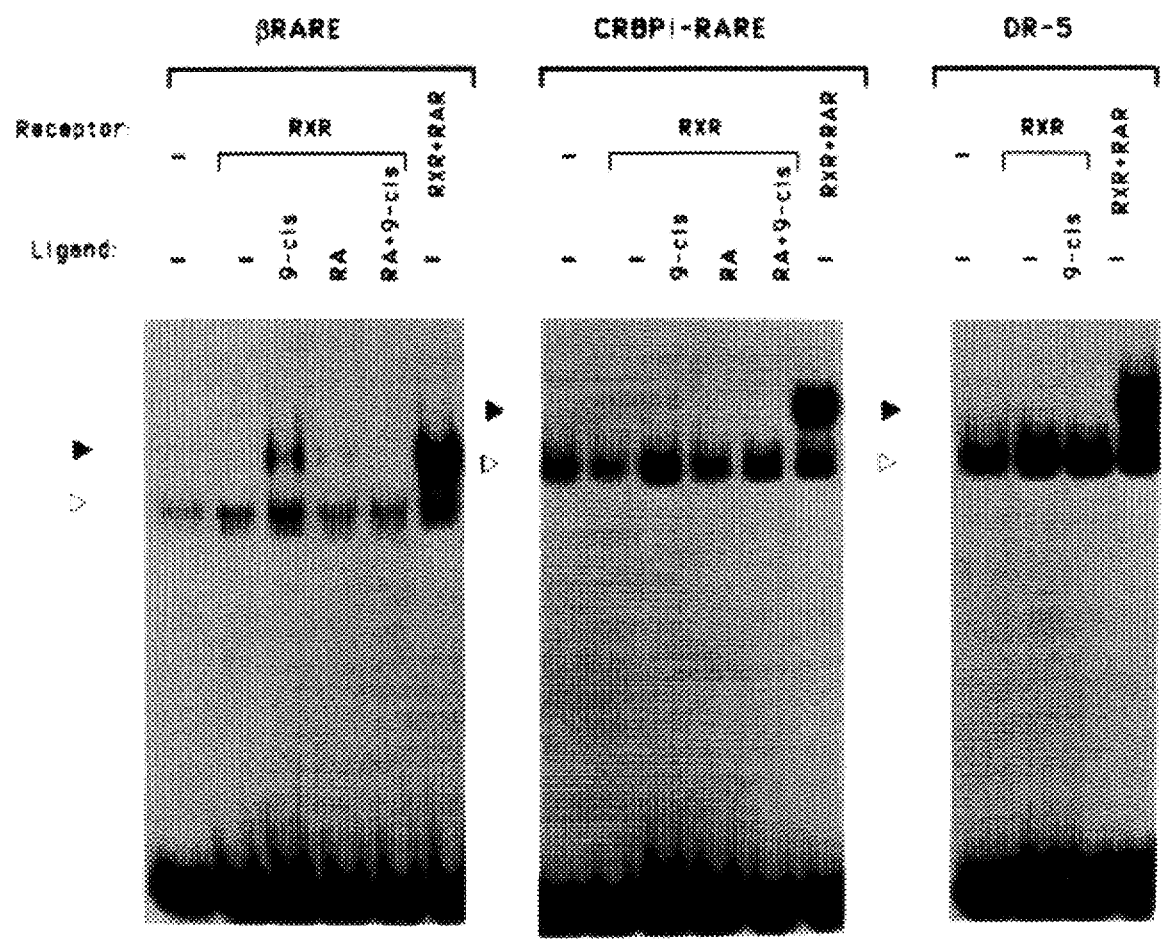
Figure 4B:
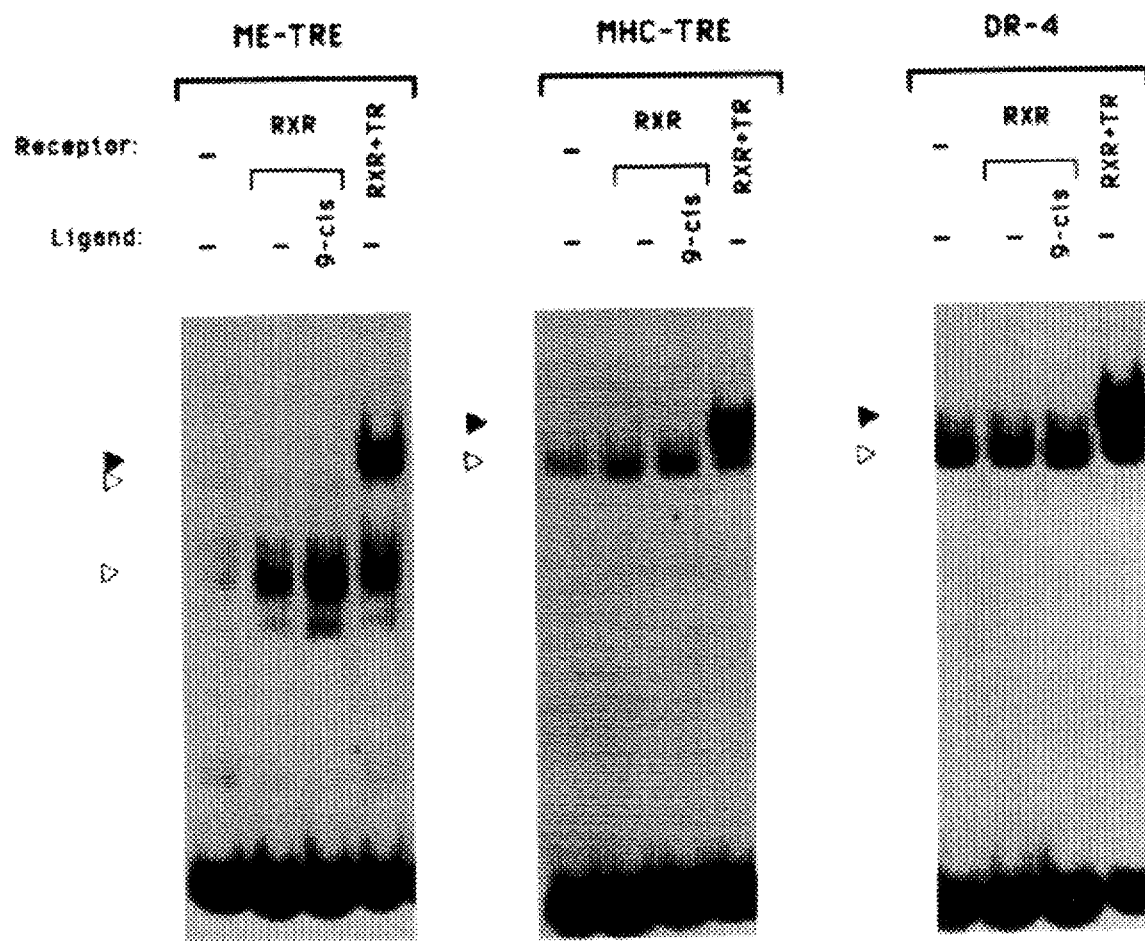

ApoAI-RARE (a direct repeat response element that contains a 2 bp spacer) which has been suggested to be RXR specific[31] resulted in a strong RXR complex in the presence of 9-cis-RA and to a lesser degree with RA ($10^{-6}M$). The RXR-RAR heterodimer also bound effectively to this response element. Since the heterodimer complex migrated at the same position as RXR homodimers, the effect of 9-cis-RA on RXR-RAR heterodimers cannot be clearly determined. RAR homodimer binding was not induced by 9-cis-RA (FIG. 3b). When we investigated 9-cis-RA induced RXR binding to another RXR responsive element[30], the CRBPII-RARE, we observed a complex that migrated more slowly than the heterodimer (in the absence of ligand), while in the presence of 9-cis-RA and RAR, both homodimer and heterodimer binding appeared to be reduced in their intensity (FIG. 3); a similar effect was seen at high RA concentrations or when both 9-cis-RA and RA were present. 9-cis-RA also induced RXR interaction with the β RARE (FIG. 4a), the RAR response element from the human RARβ promoter[35,36] that contains a 5 bp spacer. However, the RXR homodimer band was considerably weaker than the RAR-RXR heterodimer band at the protein concentrations used. Interestingly, another natural RARE derived from the rat CRBPI promoter[37], that similar to the ApoAI-RARE contains a 2 bp spacer did not show any binding of RXR in the presence of 9-cis-RA (FIG. 4a), indicating that the actual sequence of the repeated core motif is critical for RXR homodimer binding. Similarly, the DR-5-RARE, a perfect repeat element derived from the β-RARE[38] did not exhibit interaction with RXR in the presence of 9-cis-RA, while it interacted strongly with RXR when RARE was present (FIG. 4a).

Figure 4C:
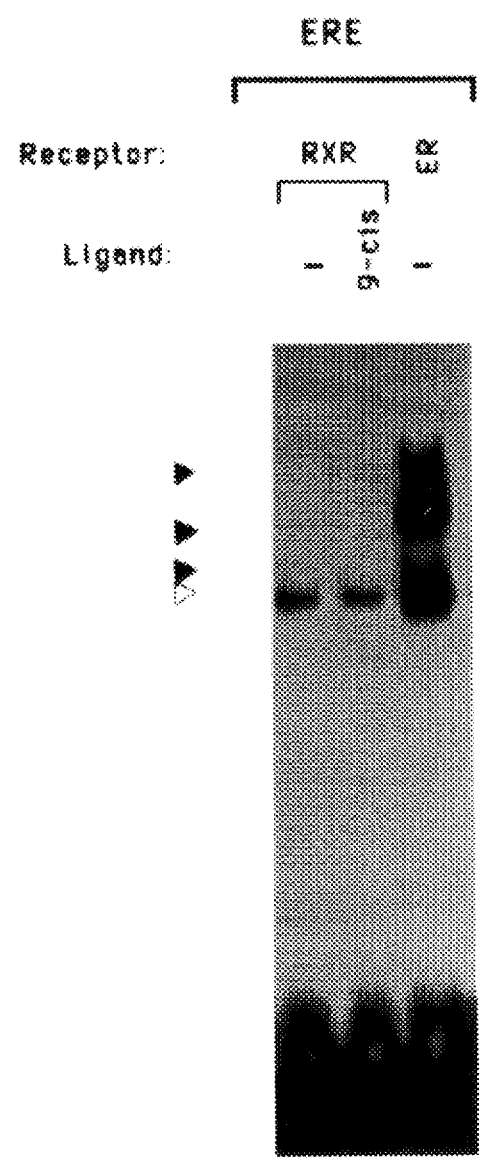

To examine whether RXR homodimer binding is specific to certain RAREs, we also performed gel shift experiments with the $T_3$ response elements from the rat α-myosin heavy chain promoter (MHC-TRE)[39], the rat malic enzyme (ME-TRE)[40] and the perfect repeat DR-4[38]. In all three cases, specific binding of RXR in the presence or absence of 9-cis-RA could not be observed, while all three response elements bound effectively TR/RXR heterodimers (FIG. 4b), consistent with the notion that these elements are not induced by retinoids. Similarly, the perfect palindromic ERE[41] also did not interact with RXR homodimers (FIG. 4c).

9-cis induced homodimer formation occurs in the absence of DNA

It was reported the RXR exists mainly as monomer in solution[16]. An important question is whether 9-cis-RA induced RXR homodimers, like the RXR containing heterodimers, can form in solution in the absence of DNA. To address this question we took advantage of the Flag-RXR derivative that can be specifically precipitated with anti-Flag antibody while RXR wild type cannot.

Flag-RXRα was cloned in frame in the expression vector pGex 2T (Pharmacia) and was expressed in bacteria using the procedure provided by the manufacturer. Protein was partially purified on a prepacked glutathione sepharose 4B column (Pharmacia) and tested for its function by gel retardation assays and western blotting using anti-Flag antibody. Immunocoprecipitation assay was performed essentially as described[26]. Briefly, 10 μl of $^{35}$S-labeled in vitro synthesized RXRα protein was incubated with 5 μl (approximately 0.1 μg) of partially purified bacterially expressed Flag-RXRα fusion protein or similarly prepared glutathione transferase control protein in 100 μl buffer containing $10^{-7}$M 9-cis-RA, 50 mM KCl and 10% glycerol for 30 min at room temperature. When assayed in the presence of chemical cross-linker or oligonucleotides, we added 2 μl of 100 mM Dithiobis succinimidylpropionate (DSP) dissolved in DMSO or 10 ng of oligonucleotide and continued the incubation at room temperature for 15 min. The reaction mixtures were then incubated with 1 μl of anti-Flag antibody or nonspecific preimmune serum for 2 h on ice. Immune complexes were precipitated by adding 50 μl of protein-A-sepharose slurry and mixing continuously in the cold room for 1 h. The immune complexes were washed extensively with cold NET-N buffer (20 mM Tris, pH 8.0, 100 mM NaCl, 1 mM DTT, 0.5% NP-40) containing $10^{-7}$M 9-cis-RA, boiled in SDS sample buffer and resolved by SDS-polyacrylamide gel electrophoresis. The gel was fixed, dried and visualized by autoradiography.

When we mixed Flag-RXR with in vitro labeled $^{35}$S-RXR protein, the labeled RXR could be coprecipitated in the presence of anti-Flag antibody but not in the presence of nonspecific serum (FIG. 5). Coprecipitation efficiency was slightly increased in the presence of the ApoAI-RARE but not in the presence of the MHC-TRE. In addition, incubation with a crosslinker (DSP) further enhanced coprecipitation of the labeled RXR. In all cases, specific coprecipitation was only observed in the presence of 9-cis-RA. These data therefore give strong support to the assumption that 9-cis-RA induced RXR homodimer formation occurs in solution and does not require RXR-DNA interaction.

Response element specific transcriptional activation by 9-cis-RA and RXRα

To investigate whether 9-cis-RA/RXRα homodimer response element interaction can be correlated with transcriptional activation of such response elements by the 9-cis-RA/RXR complex, we carried out a series of transient transfection assays in CV-1 cells, where we cotransfected receptor expression vectors with CAT reporter constructs that carried various response elements upstream of the tk promoter. CV-1 cells were transiently transfected using a modified calcium phosphate precipitation procedure as described previously[42]. CAT activity was normalized for transfection efficiency by measuring the enzymatic activity derived from the cotransfected β-galactosidase expression plasmid (pCH110, Pharmacia). The transfected cells were grown in the absence or presence of $10^{-7}$M 9-cis-RA or all-trans-RA.

Figures 6A, 6B:
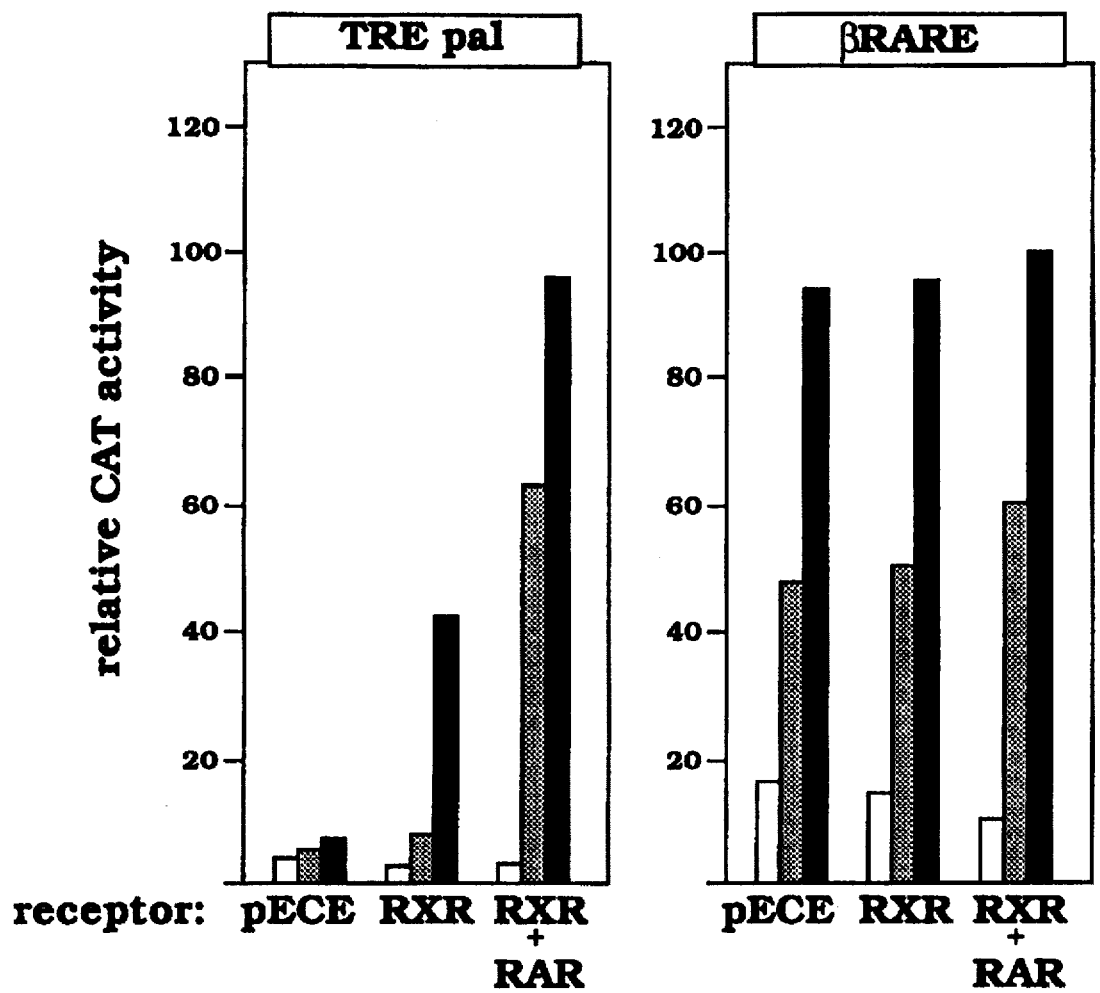
Figure 6C:
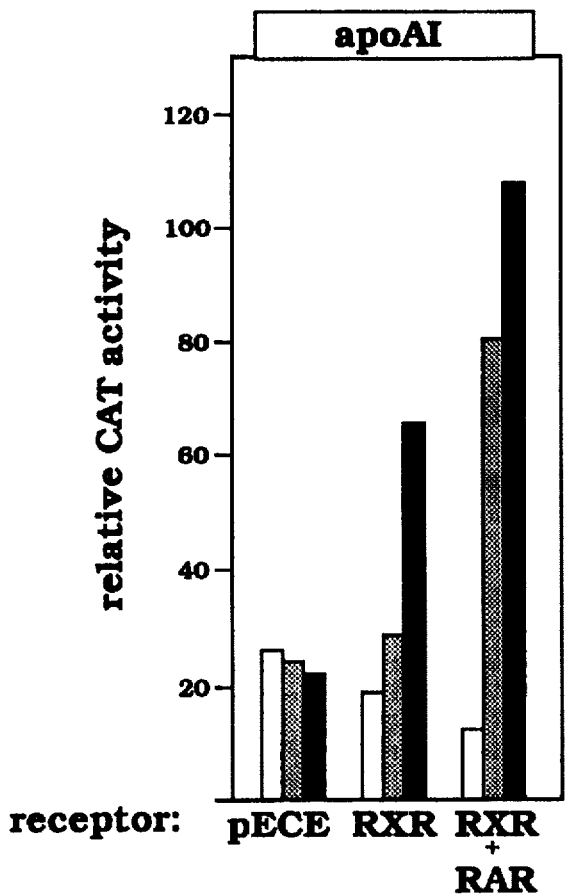
Figure 6D:
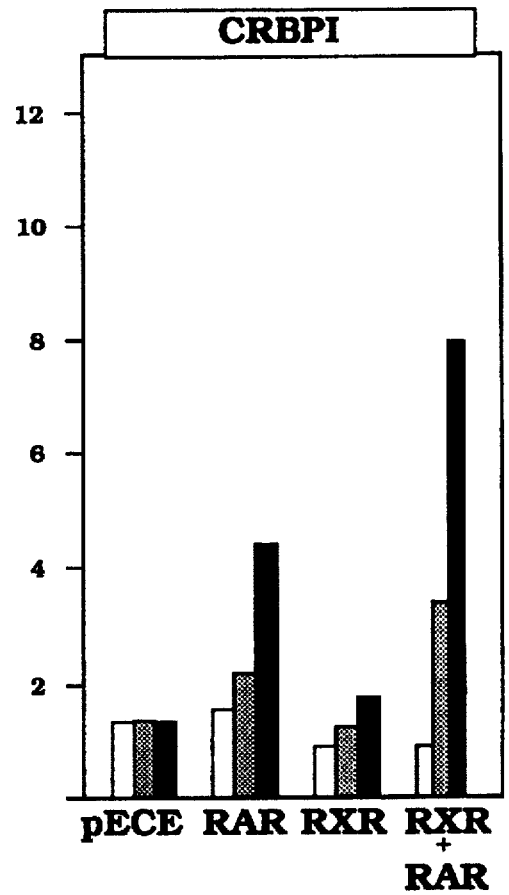

With the TREpal containing reporter, we observed strong activation by RXRα in the presence of 9-cis-RA and little activation when RA was added. Activation could be further enhanced by cotransfection of RARα. In this case, however, RA also functioned as an effective activator although not as efficiently as 9-cis-RA. Overall, activation by 9-cis-RA in the presence of RARα and RXRα was approximately twice as strong as seen with RXRα alone, consistent with the DNA binding data where binding was observed by both the heterodimer and the homodimer in the presence of 9-cis-RA when both receptors were present (FIG. 6a). When we examined the βRARE (FIG. 6b), we observed that this response element was highly activated by endogenous CV-1 cell receptors consistent with previous observations[36,41], such that further activation by low concentrations of cotransfected receptors could not be observed. Interestingly, however, 9-cis-RA was a more potent activator at $10^{-7}$M than RA. These data thus indicate that CV-1 cells contain endogenous retinoid receptor activity that is particularly active on the βRARE and is responsive to 9-cis-RA.

The ApoAI element containing reporter was also very effectively activated by RXRα in the presence of 9-cis-RA (FIG. 6c) while RA did not induce above the level obtained in the absence of RXRα. Similar to the TREpal, maximal activation was seen when both receptors RXRα and RARα were cotransfected. Under these conditions RA also led to a strong activation. In contrast, the CRBPI element, where we did not observe DNA binding by RXR in the presence of 9-cis-RA, also was not activated by RXR and 9-cis-RA in the transient transfection studies (FIG. 6d) while RARα alone led to significant activation that was mostly 9-cis-RA dependent. The heterodimer RARαRXRα allowed maximal activation in the presence of 9-cis-RA. Not unexpectedly, no induction by RXRα and 9-cis-RA was observed on the MHC-TRE, the ME-TRE or the ERE. These in vivo analyses showed a very significant correlation to the results obtained with the in vitro DNA binding studies, in that strong activation by RXRα in the presence of 9-cis-RA is only observed on the response elements that strongly interact with the 9-cis-RA induced RXRα homodimer.

9-cis retinoic acid inhibits activation by TR/RXR heterodimer

We have observed that a CAT reported gene that is activated by a thyroid hormone receptor/RXR heterodimer in the presence of thyroid hormone ($T_3$) can be inhibited by adding 9-cis-RA. This type of inhibition is most easily measured by using a transfection assay.

The preceding examples are intended to illustrate but not limit the invention. While they are typical of those that might be used, other procedures known to those skilled in the art may be alternatively employed.

Throughout this application various publications are referenced by numbers. Following is a complete citation to the publications. The disclosures of these publications in their entireties are hereby incorporated by reference into this application in order to more fully describe the state of the art to which this invention pertains.

REFERENCES

1. Lotan, R. *Biochem. Biophys. Acta* 605, 33–91 (1981).
2. Roberts, A. B., & Sporn, M. B. In: The Retinoids (M. B. Sporn, A. B. Roberts, D. S. Goodman, eds). Academic Press, Florida pp. 209–286 (1984).
3. Knudson, D. D. *J. Invest. Dermatol.* 62,288 (1974).
4. Weiss, J. S., Ellis, C. N., Headington, J. T., Tincoff, T., Hamilton, T. A., & Voorhees, J. J. *JAMA* 259, 527–532 (1988).
5. Hong, W. K., Lippman, S. M., Itri, L. M., Karp, D. D., Lee, J. S., Byers, R. M., Schantz, S. P., Kramer, A. M., Lotan, R., Peters, L. J., Dimery, I. W., Brown, B. W., & Goepfert, H. *N. Engl. J. Med.* 323, 795–804 (1990).
6. Huang, M. E., Ye, Y. C., Chen, S., Chai, J. R., Lu, J. X., Lu, L., Zhoa, L., Gu, L. j., & Wang, Z. Y. *Blood* 72, 567 (1988).
7. Petkovich, M., Brand, N. J., Krust, A., & Chambon, P. *Nature* 330, 444–450 (1987).
8. Giguere, V., Ong, E. S., Seigi, P., & Evans, R. M. *Nature* 330, 624–629 (1987).
9. Benbrook, D., Lernhardt, E., & Pfahl, M. *Nature* 333, 669–672 (1988).
10. Brand, N., Petkovich, M., Krust, A., de Thé, H., Marchio, A., Tiollais, P., & Dejean, A. *Nature* 332, 850–853 (1988).
11. Krust, A., Kastner, P. H., Petkovich, M., Zelent, A., & Chambon, P. *Proc. Nat. Acad. Sci,* U.S.A. 86, 5310–5314 (1989).
12. Giguere, V., M. Shago, R. Zirngibl, P., Tate, Rossant, J., & Varmuza, S. *Mol. Cell. Biol.* 10, 2335–2340 (1990).
13. Hamada, K., Gleason, S. L., Levi, B-Z., Hirschreid, S., Appella, E., & Ozato, K. *Proc. Natl. Acad. Sci., USA* 86, 8289–8293 (1989).
14. Mangelsdorf, D. J., Ong, E. S., Dyck, J. A., & Evans, R. M. *Nature* 345, 224–229 (1990).
15. Yu, V. C., Delsert, C., Andersen, B., Holloway, J. M., Devary, O. V., Naär, A. M., Kim, S. Y., Boutin, J-M., Glass, C. K., & Rosenreid, M. G. *Cell* 67, 1251–1266 (1991).
16. Leid, M., Kastner, P., Lyons, R., Nakshatri, H., Saunders, M., Zacharewski, T., Chen, J-Y., Staub, A., Garnier, J-M., Mader, S., & Chambon, P. *Cell* 68, 377–395 (1992).
17. Mangelsdorf, D. J., Borgmeyer, U., Heyman, R. A., Zhou, J. Y., Ong, E. S., Oro, A. E., Kakizuka, A., & Evans, R. M. *Genes & Dev.* 6, 329–344 (1992).
18. Evans, R. M. *Science* 240, 889–895 (1988).
19. Green, S., & Chambon, P. *Trends Genet.* 4, 309–314 (1988).
20. Lehmann, J. M., Hoffman, B., & Pfahl, M. *Nucl. Acids Res.* 19, 573–578 (1991).
21. Leroy, P., Krust, A., Zelent, A., Mendelsohn, C., Garnier, J-M., Kastner, P., Dierich, A., & Chambon, P. *EMBO J.* 10, 59–69 (1991).
22. Zelent, A., Mendelsohn, C., Kastner, P., Krust, A., Garnier, J-M., Ruffenach, F., Leroy, P., & Chambon, P. *EMBO J.* 10, 71–81 (1991).
23. Oro, A. E., McKeown, M., & Evans, R. M. *Nature* 347, 298–301 (1990).
24. Heyman, R., Mangelsdorf, D. J., Dyck, J. A., Stein, R. B., Eichele, G., Evans, R. M., & Thaller, C. *Cell* 68, 397–406 (1992).
25. Levin, A. A., Sturzenbecker, L. J., Kazmer, S., Bosakowski, T., Huselton, C., Allenby, G., Speck, J., Kratzeisen, C., Rosenberger, M., Lovey, A., & Grippo, J. F. *Nature* 355, 359–361 (1992).
26. Zhang, X-k., Hoffmann, B., Tran, P., Graupner, G., & Pfahl, M. *Nature* 355, 441–446 (1992).
27. Kliewer, S. A., Umesono, K., Mangelsdorf, D. J., & Evans, R. M. *Nature* 355, 446–449 (1992).
28. Marks, M. S., Hallenbeck, P. L., Nagata, T., Segars, J. H., Apella, E., Nikodem, V. M., & Ozato, K. *EMBO J.* 11, 1419–1435 (1992).
29. Bugge, T. H., Pohl, J., Lonnoy, O., & Stunnenberg, H. G. *EMBO J.* 11, 1409–1418 (1992).
30. Mangelsdorf, D. J., Umesono, K., Kliewer, S. A., Borgmeyer, U., Ong, E. S., & Evans, R. M. *Cell* 66, 555–561 (1991).
31. Rottman, J. N., Widom, R. L., Nadal-Ginard, B., Mahdavi, V., & Karathanasis, S. K. *Mol. Cell. Biol.* 11, 3814–3820 (1991).
32. Hermann, T., Hoffmann, B., Zhang, X-k., Tran, P. & Pfahl, M. *Mol. Endrinol.* (accepted for publication).
33. Zhang, X-k., Tran, P., & Pfahl, M. *Mol. Endocrinol.* 5, 1909–1920 (1991b).
34. Glass, C. K., Holloway, J. M., Devary, O. V., & Rosenfeld, M. G. *Cell* 54, 313–323 (1988).
35. de Thé, H., Vivanco-Ruiz, M. M., Tiollais, P., Stunnenberg, H., & Dejean, A. *Nature* 343, 177–180 (1990).
36. Hoffmann, B., Lehmann, J. M., Zhang, X-k., Hermann, T., Graupner, G., & Pfahl, M. *Mol. Endocrinol.* 4, 1734–1743 (1990).
37. Husmann, M. B., Hoffmann, B., Stump, D. G., Chytil, F., & Pfahl, M. (submitted) (1992).
38. Umesono, K., Murakami, K. K., Thompson, C. C., & Evans, R. M. *Cell* 65, 1255–1266 (1991).
39. Flink, I. L., & Morkin, E. *J. Biol. Chem.* 265, 11233–11237 (1990).
40. Desvergne, B., Petty, K. J., & Nikodem, V. M. *J. Biol. Chem.* 266, 1008–1013 (1991).
41. Klein-Hitpass, L., Schorpp, M., Wagner, U., & Ryffel, G. U. *Cell* 46, 1053–1061 (1986).
42. Husmann, M., Lehmann, J., Hoffmann, B., Hermann, T., Tzukerman, M., & Pfahl, M. *Mol. Cell. Biol.* 11, 4097–4103 (1991).
43. Tora, L., White, J., Brou, C., Tasset, D., Webster, N., Scheer, E., & Chambon, P. *Cell* 59, 477–487 (1989).
44. Tzukerman, M., Zhang, X-k., Wills, K. N., Graupner, G., Hermann, T., & Pfahl, M. *New Biol.* 2, 613–620 (1990).
45. Zhang, X-k., Wills, K. N., Graupner, G., Tzukerman, M., Hermann, T., & Pfahl, M. *New Biol* 3, 1–14 (1991a).
46. Yen, P. M., Darling, D. S., Carter, R. L., Forgione, M., Umeda, P. K., & Chin, W. W. *J. Biol. Chem.* 267, 3565–3568 (1992).
47. Forman, B. M., & Samuels, H. H. *Mol. Endocrinol.* 4, 1293–1301 (1990).
48. Zenke, M., Munoz, A., Sap, J., Vennstrom, B., & Beug, H. *Cell* 61, 1035–1049 (1990).
49. Yang-Yen, H-F., Zhang, X-k., Graupner, G., Tzukerman, M., Sakamoto, B., Karin, M., & Pfahl, M. *New Biol.* 3, 1206–1219 (1991).

What is claimed is:

1. A method of screening a substance for the ability to affect the formation of a functional retinoid X receptor homodimer, which affects the activation of transcription by the homodimer comprising combining the substance and a solution containing retinoid X receptors and determining the presence of homodimer formation in solution by either 1) a gel shift assay utilizing a response element to bind the homodimer or 2) coprecipitation, the presence of homodimer formation indicating a substance that can affect the activation of transcription.

2. The method of claim 1, wherein the effect is the induction of homodimer formation.

3. The method of claim 1, wherein the retinoid X receptor is retinoid X receptor α.

4. The method of claim 1, wherein the presence of homodimer formation is detected by said coprecipitation and said coprecipitation is resolved by a denaturing gel electrophoresis assay.

5. The method of claim 1, wherein the presence of homodimer formation is detected by said gel shift assay and said gel shift assay is resolved under non-denaturing conditions.

6. A method of screening a substance for the ability to inhibit the formation of a retinoid X receptor homodimer, which affects the activation of transcription by the homodimer, comprising the steps of:

a. contacting in a first solution, retinoid X receptors and a ligand under conditions that allow retinoid X receptor homodimer formation;

b. determining a first amount of retinoid X receptor homodimer formation in said first solution by a method selected from the group consisting of 1) a gel shift assay utilizing a response element to bind the homodimer and 2) coprecipitation;

c. contacting in a second solution, retinoid X receptors, a ligand and a substance under said conditions of step a);

d. determining a second amount of retinoid X receptor homodimer formation in said second solution by the method selected in step b); and e. thereafter comparing said first amount of retinoid X receptor homodimer formation and said second amount of retinoid X receptor homodimer formation, wherein a determination that said first amount is greater than said second amount indicates said substance inhibits the formation of a retinoid X receptor homodimer, the inhibition of homodimer formation indicating a substance that can affect the activation of transcription.

7. A method of screening a response element for binding with a retinoid X receptor homodimer, comprising combining in solution the response element with the retinoid X receptor homodimer complexed with a ligand selected from the group consisting of 9-cis-RA and all-trans-RA, and detecting the presence of binding by a gel shift assay.

8. The method of claim 7, wherein said gel shift assay is resolved under non-denaturing conditions.

* * * * *